United States Patent
Morgan et al.

(10) Patent No.: US 7,915,036 B2
(45) Date of Patent: Mar. 29, 2011

(54) COMPOSITIONS COMPRISING T CELL RECEPTORS AND METHODS OF USE THEREOF

(75) Inventors: Richard A. Morgan, Columbia, MD (US); Steven A. Rosenberg, Potomac, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 706 days.

(21) Appl. No.: 11/575,077

(22) PCT Filed: Sep. 13, 2004

(86) PCT No.: PCT/US2004/029608
§ 371 (c)(1),
(2), (4) Date: Mar. 29, 2007

(87) PCT Pub. No.: WO2006/031221
PCT Pub. Date: Mar. 23, 2006

(65) Prior Publication Data
US 2009/0053184 A1 Feb. 26, 2009

(51) Int. Cl.
*C07H 21/04* (2006.01)
*C12N 15/00* (2006.01)
*A61K 48/00* (2006.01)
*C07K 14/00* (2006.01)
*C12N 1/20* (2006.01)

(52) U.S. Cl. .................. 435/320.1; 514/44 R; 536/23.5

(58) Field of Classification Search ........................ None
See application file for complete search history.

(56) References Cited

U.S. PATENT DOCUMENTS

| 5,830,755 A | 11/1998 | Nishimura et al. |
| 6,805,861 B2 | 10/2004 | Stauss |
| 7,135,560 B1 | 11/2006 | Doucette-Stamm et al. |
| 2005/0009180 A1* | 1/2005 | Yang et al. ................ 435/455 |

FOREIGN PATENT DOCUMENTS
WO   WO 02/00174 A2   1/2002

OTHER PUBLICATIONS

Engel et al (Cell, 1988, 54(4): 473-484).*
Lim et al (J. Immunol. 2000, 165: 2001-2011).*
Gao et al (J. Immunother. 23: 643-653, 2000).*
Morel et al (Immunity 12:107-117, 2000).*
den Eynde and Morel (Cur. Opin. Immunol. 13: 147-153, 2001).*
Alberts et al (Molecular Biology of the Cell, 2nd Ed., 1989, Garland Publishing, Inc. NY & London, p. 1037).*
Janeway-Travers (Immunobiology, 3rd Edition, 1997, pp. 4:33-4:37).*
Hawes et al (J. Immunol. 1995, 154: 555-566).*
Bownds et al., *J. Immunotherapy*, 24, 1-9 (2001).
Clay et al., *J. Immunology*, 163, 507-513 (1999).
Denkberg et al., *J. Immunology*, 167, 270-276 (2001).
Dudley at al., *J. Immunotherapy*, 24, 363-373 (2001).
Dudley at al., *J. Immunotherapy*, 25(3), 243-251 (2002).
Dudley at al., *Science*, 298, 850-854 (2002).
Kessels et al., *Nature Immunology*, 2, 957-961 (2001).
Morgan et al., *J. Immunology*, 171, 3287-3295 (2003).
Rosenberg et al., *Proc. Nat'l. Acad. Sci.*, 101(Suppl. 2), 14639-14645 (2004).
Rubinstein et al., *J. Immunology*, 170, 1209-1217 (2003).
Schaft et al., *J. Immunology*, 170, 2186-2194 (2003).
Stanislawski et al., *Nature Immunology*, 2, 962-970 (2001).
Tsuji at al., *Cancer Sci.*, 94, 389-393 (2003).
Zeng et al., *Cancer Research*, 62, 3630-3635 (2002).
Zhao et al., 45th ASH Annual Meeting Abstract (2003).
GENBANK Accession No. AX366046, Feb. 15, 2002.
GENBANK Accession No. ABL49292, Dec. 6, 2006.

* cited by examiner

*Primary Examiner* — Michael Szperka
*Assistant Examiner* — Marianne Dibrino
(74) *Attorney, Agent, or Firm* — Leydig, Voit & Mayer

(57) ABSTRACT

Nucleic acids encoding antitumor TCRs recognizing MART-1, NY-ESO-1, and melanoma gp100 peptides; vectors and cells comprising the same; and methods of using the foregoing.

11 Claims, No Drawings

US 7,915,036 B2

COMPOSITIONS COMPRISING T CELL RECEPTORS AND METHODS OF USE THEREOF

CROSS-REFERENCE TO RELATED PATENT APPLICATIONS

This application is the U.S. national phase of International Patent Application No. PCT/US04/29608, which was filed on Sep. 13, 2004.

FIELD OF THE INVENTION

This invention pertains to T cell receptors against tumor-associated antigens, nucleic acids encoding the same, vectors and cells comprising the nucleic acids encoding the T cell receptors, and methods of use thereof.

BACKGROUND OF THE INVENTION

Cancer patients, e.g., melanoma patients, can be effectively treated by using adoptive immunotherapy. In one adoptive immunotherapy method, a population of white blood cells comprising T cells that react with the cancer cells is isolated from the patient's tumor, grown to large numbers in vitro, and returned to the patient. The protein on the surface that recognizes the tumor (i.e., primarily provides specificity to the T cell:tumor cell interaction) is the T cell receptor. Naturally occurring T cell receptors comprise two subunits, an α-subunit and a β-subunit, and each is a unique protein produced by recombination event in each T cell's genome.

MART-1, NY-ESO-1, and gp100 are tumor-associated antigens known in the art. For example, MART-1 is described by Clay et al., *J. Immunol.*, 163, 507-513 (1999), and U.S. Patent Application Publication No. 2003/0144482 A1; NY-ESO-1 is described by Zeng et al., *Cancer Research*, 62, 3630-3635 (2002) (and references therein); and "gp100" is described by Morgan et al., *J. Immunol.*, 171, 3287-3295 (2003) (and references therein) and U.S. Patent Application Publication No. 2003/0144482 A1.

Dudley et al. (*Science*, 298, 850-854 (2002)) showed that the adoptive transfer of highly-selected tumor-reactive T cells directed against self-derived tumor antigens after nonmyeloablative conditioning of patients with metastatic cancer can cause persistent clonal repopulation of T cells. These T cells can proliferate in vivo, display functional activity, and traffic to tumor sites (Dudley et al. (2000)). Consequently, these T cells can cause the regression of metastatic cancer, as well as initiate autoimmunity-mediated cancer-cell destruction. This reference also disclosed that high doses of IL-2 facilitated immunotherapy.

Unfortunately, however, the generation of cancer-reactive lymphocytes is sometimes challenging, and until now, expensive and labor intensive.

It is also desirable to have a variety of T cells available to provide an array of tools to better treat cancer patients. The challenges and expense of generating these T cells, however, places practical restrictions on the number of types of T cells available for adoptive transfer and immunotherapy of patients in need.

Fortunately, the invention mitigates some of the challenges described above. Uses, features, and advantages of the invention will be apparent from the detailed description provided herein.

BRIEF SUMMARY OF THE INVENTION

The invention provides nucleic acids encoding polypeptides that are capable of forming a subunit of a T cell receptor (TCR). The TCR subunits have the ability to form TCRs that confer specificity to T cells for tumor cells presenting MART-1, NY-ESO-1, and melanoma-related gp100. These subunits consist essentially of amino acid sequences provided in SEQ ID NOS: 2, 4, 6, 8, 10, and 12, and confer upon T cells expressing them a high-avidity and reactivity toward suitable cancer cells. The subunits do not need to have exactly the sequences provided in SEQ ID NOS: 2, 4, 6, 8, 10, and 12, but can vary therefrom provided that the subunits retain the ability to form TCRs conferring upon transfected T cells the ability to home to tumor cells, and participate in immunologically-relevant cytokine signaling. The derivative TCRs preferably also bind target cells displaying the relevant tumor-associated peptide with high avidity, and optionally mediate efficient killing of target cells presenting the relevant peptide in vivo, in vitro, or both in vivo and in vitro.

The nucleic acids encoding these polypeptide's are, preferably isolated from their natural context in a (naturally-occurring) chromosome of a T cell, and can be incorporated into suitable vectors. Both the nucleic acids and the vectors comprising them usefully can be transferred into a cell, which cell is preferably a T cell.

The nucleic acids and cells of the invention also can be incorporated into pharmaceutically acceptable compositions, or alternatively formulated with other reagents to form a composition suitable for administration to a human or other mammal.

Compositions of the invention can also be used to form medicaments useful in treating or preventing cancer in a mammal in need of therapy or protection. These medicaments can be used to treat or protect a mammal, which is preferably a human. These medicaments are also useful in the study of immune-related ablation of cancer, and when complexed with a labeling moiety can be used as imaging agents or detection agents to visualize or detect target cells.

DETAILED DESCRIPTION OF THE INVENTION

The invention provides compositions, and methods of using the same, that enable more convenient immunotherapy of cancer patients. Advantageously, the invention provides an off-the-shelf composition allowing rapid modification of a mammal's own T cells (or those of another mammal) to rapidly and easily produce modified T cells having excellent cancer cell killing properties. While it is convenient to remove the cells from a mammal to be treated prior to contacting the cells with the nucleic acids or vectors of the invention, the nucleic acids and vectors of the invention also can be transferred into a mammal's cells while in the mammal's body.

The invention provides a nucleic acid encoding a chain of a T cell receptor (TCR) having excellent anti-cancer properties, as well as combinations of such nucleic acids, vectors comprising these nucleic acids, and the cells produced thereby. The invention also provides a method of causing the substantial regression of a metastatic tumor in vivo using T cells modified to express a TCR that is not encoded by the T cells innate genome prior to treatment in accordance with the invention. Each of these preferred embodiments is more fully described below.

White blood cells can be obtained from a mammal and contacted with one or more nucleic acids encoding a protein that is essentially one or more T cell receptor (TCR) chains or subunits (i.e., at least an α-chain or a β-chain) identified by SEQ ID NO: 2, 4, 6, 8, 10, and/or 12 under suitable conditions that enable the nucleic acid to be transferred into the white blood cells to produce modified T cells. The modified T cells are then able to express one or more chains of a TCR (and preferably two chains) encoded by the transduced nucleic acid or nucleic acids. Preferably, the modified T cells produce an exogenous TCR. The essential aspect of the TCR is that it has high avidity for a tumor antigen presented by an major histocompatibility complex (MHC) or similar immunological component. This preferably results in the T cell being capable of producing at least 600 pg/ml of interferon gamma, and more preferably at least 1000 pg/ml when exposed to low levels of peptide (<10 ng/ml) when measured by the methods disclosed in Example 1, Dudley et al., *J. Immunotherapy* 22:288-298 (1999) and Dudley et al., *The Cancer Journal* 6:69-77 (2000). T cells expressing at least 1000 pg/ml of interferon gamma when exposed to low levels of target peptide, are deemed to participate in immunologically relevant cytokine signaling.

The protein encoded by the inventive nucleic acids can be expressed with additional polypeptides attached to the amino-terminal or carboxyl-terminal portion of the inventive α-chain or β-chain of a TCR so long as the attached additional polypeptide does not interfere with the ability of the α-chain or β-chain to form a functional T cell receptor. Typically, the fused additional sequences will be cleaved from the inventive α-chain or a β-chain prior to its participation in mediating an immunological reaction.

The T cells are preferably obtained from the mammal to which the modified T cells are likely to be transferred, but this is optional. Additionally, it is convenient to use peripheral blood lymphocytes, which can be obtained directly in an aliquot of blood, or can be partially purified. However, other sources of lymphocytes are also acceptable such as (without limitation) tumor infiltrating lymphocytes (TIL), and cells obtained from other body fluids, including without limitation lymph, or lymph nodes. The modified T cells can be administered to a mammal in need of treatment or prophylaxis for cancer, with or without further manipulation, used in vitro to enrich a population of cells for noncancerous cells, or can be stored under suitable conditions for future use. Methods of culturing T cells in vitro are well known (see, e.g., Kawakami et al., *J. Immunol.*, 142, 3452-3461 (1989)). Additionally, the modified T cells can be used to study the immunological ablation of cancer, and can be complexed with a labeling moiety to produce a reagent capable of visualizing or detecting a target cell.

A mammal can be treated or protected against a cancerous condition by transferring the nucleic acids of the invention into cells of the mammal in vivo because T cells comprising the nucleic acids of the invention can home to a tumor, participate in cytokine signaling, and undergo clonal expansion in the presence of a suitable tumor. Nonetheless, it is preferable to transfer the nucleic acids of the invention to mammalian cells ex vivo or in vitro.

When cells transduced by the inventive nucleic acids or inventive vectors are administered to a mammal, the mammal is preferably human, and the cells are preferably administered via intravenous infusion. Additionally, when, the inventive transduced cells are administered to a human, the human preferably is first treated with nonmyeloablative lymphodepletion chemotherapy (e.g., see, Dudley et al., *J. Immunother.*, 25, 243-251 (2002). While not desiring to be bound by any particular theory, it is believed that nonmyeloablative lymphodepletion chemotherapy prior to administration of the modified T cells attenuates natural homeostatic mechanisms that tend to prevent excessive lymphocyte accumulation in the mammal. Additionally, the treated mammal is preferably also treated with IL-2, and more preferably a high-dose of IL-2. Without desiring to be bound by any particular theory it is believed that the high-dose of IL-2 encourages proliferation of the modified T cells in the mammal.

The nucleic acids encoding the TCR can be an α-chain or β-chain of a T cell receptor or both or a portion thereof. The TCR amino acid sequences provided in SEQ ID NOS: 2 and 4; 6 and 8; and 10 and 12, have been found to encode TCRs with a surprisingly high avidity for antitumor antigens presented by an antigen presenting cell (APC), and confer good ability to attack cancer cells that present tumor associated antigens in the context of a major histocompatibility complex (MHC). Accordingly, transfer of nucleic acids capable of expressing polypeptides having SEQ ID NOS: 2 and 4; 6 and 8; or 10 and 12 into a T cell, or into a population of white blood cells comprising T cells, yields T cells capable of destroying cancer cells, which cancer cells are preferably melanoma cells, and more preferably are metastatic melanoma cells. SEQ ID NOS: 2 and 4 form the α- and β-chains of an anti-MART-1 TCR, SEQ ID NOS: 6 and 8 form the α- and β-chains of an anti-NY-ESO-1 TCR, and SEQ ID NOS: 10 and 12 form the α- and β-chains of an anti-melanoma tumor antigen gp100 TCR. T cells expressing these TCRs have been found to proliferate in vivo, display functional activity, and traffic to tumor sites as is illustrated in the examples herein. When nucleic acids capable of expressing polypeptides having SEQ ID NOS: 2 and 4; 6 and 8; or 10 and 12 into a T cell, or into a population of white blood cells comprising T cells, preferably yields T cells capable of producing at least 600 pg/ml, and more preferably at least 1000 pg/ml when exposed to low levels of target peptide under suitable conditions (see, e.g., Dudley et al., *J. Immunotherapy* 22:288-298 (1999) and Dudley et al., *The Cancer Journal* 6:69-77 (2000)). Additionally, T cells that have received nucleic acids of the invention such that they express polypeptides consisting of SEQ ID NOS: 2 and 4, or SEQ ID NOS: 6 and 8, or SEQ ID NOS: 10 and 12 are capable of causing the regression of tumors in vivo. The nucleic acids of the invention can comprise natural nucleotides, modified nucleotides, analogs of nucleotides, or mixtures of the foregoing so long as they are capable of causing the expression of a polypeptide in vitro, and preferably, in a T cell. The nucleic acids of the invention are preferably RNA, and more preferably DNA.

The polypeptide of SEQ ID NO: 2 was isolated from a cell that produced it from TRAV35/TRAJ49/TRAC (using the nomenclature of the international ImMunoGeneTics Database). The polypeptide of SEQ ID NO: 4 was isolated from a cell that produced it from TRBV10-3/TRBD1/TRBJ1. Other products of these genes, or that can be encoded by these genes (e.g., variants of these combinations produced by genetic engineering techniques), are particularly useful, for example, in destroying cancer cells, in vivo or in vitro, and can be routinely isolated or produced. Moreover, these additional polypeptides can be routinely evaluated in accordance with the techniques set forth in the Examples provided herein. Variants of the polypeptides of SEQ ID NO: 2 and 4 preferably produce a TCR having about the same or better affinity for the tumor-associated antigen presented in the context of an MHC as that of SEQ ID NOS: 2 and 4. For example, the dissociation constant for binding between the TCR produced from a suitable variant of SEQ ID NOS: 2 and/or 4 is preferably not more than $10^2$ μM greater, and more preferably not more than $10^1$ μM greater, than the dissociation constant observed for a TCR produced from SEQ ID NOS: 2 and 4. A suitable measure of this affinity is the ability of a TCR containing a variant of SEQ ID NO: 2 or SEQ ID NO: 4 or both to kill HLA-A2$^+$ cells presenting a suitable MART-1 peptide. This killing ability of T cells transduced with the inventive nucleic acids is preferably at least 30%, more preferably at least 50%, and even more preferably at least 75%, as effective in vitro, as T cells transduced with SEQ ID NOS: 2 and 4. The average avidity for target cells (presenting the tumor associated antigen) of a population of T cells transfected by nucleic acids encoding the inventive TCR preferably increases by a at least $10^4$-fold, and more preferably by at least $10^5$ fold. Variant TCRs produced in accordance with the invention may also gain killing efficiency with routine optimization such that HLA-A2+(presenting the MART-1 peptide) cell killing efficiency may be substantially the same, or even greater than the killing efficiency of a population of T cells transduced with nucleic acids encoding non-variant. Such routine optimization can include optimization of expression levels, optimization of avidity for target cells, or both.

The polypeptide of SEQ ID NO: 6 was isolated from a cell that produced it from TRAV 17. The polypeptide of SEQ ID NO: 8 was isolated from a cell that produced it from TRBV 12-4. Variants of the polypeptides of SEQ ID NOS: 6 and 8 preferably produce a TCR having about the same or better affinity for the tumor-associated antigen presented in the context of an MHC as that of SEQ ID NOS: 6 and 8. For example, the dissociation constant for binding between the TCR produced from a suitable variant of SEQ ID NOS: 6 and/or 8 is preferably not more than $10^2$ μM greater, and more preferably not more than $10^1$ μM greater, than the dissociation constant observed for a TCR produced from SEQ ID NOS: 6 and 8. A suitable measure of this affinity is the ability of a TCR containing a variant of SEQ ID NO: 2 or SEQ ID NO: 4 or both to kill HLA-A2$^+$ cells presenting NY-ESO-1 p157-165 (SLL-MWFTQC) (SEQ ID NO: 13). This killing ability of T cells transduced with the inventive nucleic acids is preferably at least 30%, more preferably at least 50%, and even more preferably at least 75%, as effective in vitro, as T cells transduced with SEQ ID NOS: 6 and 8. The average avidity for target cells (presenting the tumor associated antigen) of a population of T cells transfected by nucleic acids encoding the inventive TCR preferably increases by a at least $10^4$-fold, and more preferably by at least $10^5$ fold. Variant TCRs produced in accordance with the invention may also gain killing efficiency with routine optimization such that HLA-A2$^+$ (presenting the NY-ESO-1 peptide) cell killing efficiency may be substantially the same, or even greater than the killing efficiency of a population of T cells transduced with nucleic acids encoding non-variant. Such routine optimization can include optimization of expression levels, optimization of avidity for target cells, or both.

The polypeptide of SEQ ID NO: 10 was isolated from a cell that produced it from, among other TCR genes, TRAV41 and the polypeptide of SEQ ID NO: 12 was isolated from a cell that produced it from, among other TCR genes, TRBV12-3. Variants of the polypeptides of SEQ ID NOS: 10 and 12 preferably produce a TCR having about the same or better affinity for the tumor-associated antigen presented in the context of an MHC as that of SEQ ID NOS: 10 and 12. For example, the dissociation constant for binding between the TCR produced from a suitable variant of SEQ ID NOS: 10 and/or 12 is preferably not more than $10^2$ μM greater, and more preferably not more than $10^1$ μM greater than the dissociation constant observed for a TCR produced from SEQ ID NOS: 10 and 12. A suitable measure of this affinity is the ability of a TCR containing a variant of SEQ ID NO: 10 or SEQ ID NO: 12 or both to kill HLA-A2$^+$ cells presenting a suitable gp100 peptide. This killing ability of T cells transduced with the inventive nucleic acids is preferably at least 30%, more preferably at least 50%, and even more preferably at least 75% as effective in vitro, as T cells transduced with SEQ ID NOS: 10 and 12. Variant TCRs produced in accordance with the invention may also gain killing efficiency with routine optimization such that HLA-A21+ (presenting the gp-100 peptide) cell killing efficiency may be substantially the same, or even greater than the killing efficiency of a population of T cells transduced with nucleic acids encoding non-variant. The average avidity for target cells (presenting the tumor associated antigen) of a population of T cells transfected by nucleic acids encoding the inventive TCR preferably increases by a at least $10^4$-fold, and more preferably by at least $10^5$ fold. Such optimization can include optimization of expression levels, optimization of avidity for target cells, or both.

As noted above, the amino acid sequences of SEQ ID NOS: 2, 4, 6, 8, 10, and 12 can be readily varied or altered without substantially diminishing (or altering) the ability of the encoded polypeptide to form part of a TCR that recognizes tumor associated antigens in the context of an MHC, and thereby facilitate destruction of a cancer cell, and preferably facilitate the regression of a tumor, lymphoma, or other cancerous state. For example, conservative and non-conservative variations can be made in complimentarity determining and non-complimentarity determining regions of the amino acid sequence of the TCR chain that do not affect function. Changes in the region of the CDR3, or within CDR3 are preferred.

The concept of "conservative amino acid substitutions" is understood by the skilled artisan, and preferably means that codons encoding positively-charged residues (H, K, and R) are substituted with codons encoding positively-charged residues, codons encoding negatively-charged residues (D and E) are substituted with codons encoding negatively-charged residues, codons encoding neutral polar residues (C, G, N, Q, S, T, and Y) are substituted with codons encoding neutral polar residues, and codons encoding neutral non-polar residues (A, F, I, L, M, P, V, and W) are substituted with codons encoding neutral non-polar residues. These variations can spontaneously occur, be introduced by random mutagenesis, or can be introduced by directed mutagenesis. Similarly, it is known in the art that spacer amino acid sequences that add 1, 2, 3, about 5, about 10, 11-20, 21-35, and more amino acids to SEQ ID NOS: 2, 4, 6, 8, 10, and 12, and deletions that remove 1, 2, 3, up to about 5, up to about 10, between 11 and 20, and between 21 and 35 amino acids from SEQ ID NOS: 2, 4, 6, 8, 10, and 12, can be made without destroying the essential characteristics of these polypeptides, which are to recognize antitumor antigens in the context of an MHC with high avidity so as to enable the destruction of cancer cells, and preferably enabling the regression of a tumor, lymphoma, or other cancerous-state. The ordinarily skilled artisan can readily and routinely screen variant amino acids and/or the nucleic acids encoding them to determine if these variations substantially lessen or destroy the cancer-destroying functionality of these sequences by methods known in the art or by methods illustrated in the Examples provided below.

The amino acid sequences that vary from SEQ ID NOS: 2, 4, 6, 8, 10, and 12 provided herein preferably have at least 60% sequence identity, more preferably at least 85% sequence identity, even more preferably at least 92% sequence identity, and optionally at least 96% sequence identity to SEQ ID NOS: 2, 4, 6, 8, 10, and 12. Also provided are amino acid sequences, and nucleic acid sequences encoding the same in which, the hypervariable or complementarity determining regions or both of SEQ ID NOS: 2, 4, 6, 8, 10, and 12 are engineered into other TCR genes such that the obtained amino acid sequence has 100% identity with one of SEQ ID NOS: 2, 4, 6, 8, 10, and 12 for at least 8, and preferably at least 12 amino acids, in at least three regions of the obtained amino acid sequence, and when expressed in normal T cells (which prior to expression of the obtained amino acid sequence; do not recognize tumor cells) allow the T cell to attack cancer cells and preferably allow the T cell to cause the regression of a tumor, lymphoma, or other cancerous state.

The invention further provides nucleic acids encoding for the polypeptides comprising and/or consisting essentially and/or consisting of SEQ ID NOS: 2, 4, 6, 8, 10, and 12 and the variants and analogs of the same described above by methods described herein and/or known in the art. Some preferred nucleic acids encoding SEQ ID NOS: 2, 4, 6, 8, 10, and 12 are those of disclosed in SEQ ID NOS: 1, 3, 5, 7, 9, and 11, respectively. Many other nucleic acids, however, are also provided by the invention. It will be readily appreciated that the redundancy of the genetic code, and the ability to readily introduce natural or synthetic introns into these sequences, to append non-coding sequences including without limitation promoters, spacer nucleic acids, IRESs, polyadenylation sequences, nuclear receptor response elements, viral encapsidation sites, and transposons, as well as many other similar and dissimilar modifications and the amino acids encoded thereby, are contemplated by and encompassed within the invention described herein. Moreover, the inventive nucleic acids can encode a pre-protein in which a portion of the protein is removed to yield an polypeptide having an amino acid sequence of the invention (i.e., of SEQ ID NO: 2, 4, 6, 8, 10, 12, or the like). Similarly, directed evolution by known methods and routine screening provides analogs and derivatives of the TCRs and the nucleic acids encoding the same by straightforward and predictable methods.

For example, the inventive nucleic acids can be mutated to derive other useful α- and β-chains of T cell receptors capable of transforming T lymphocytes useful in the context of the invention. For example, the nucleic acids of SEQ ID NOS: 1, 3, 5, 7, 9, and 11 can be used to generate a library of mutant nucleic acids. One preferred method of generating this library is to clone a portion of one or more nucleic acids of SEQ ID NOS: 1, 3, 5, 7, 9, and 11 into a vector and propagating the same in the *E. coli* mutator strain XL1-Red (available from Strategene, La Jolla, Calif.). A library of yeast cells can be generated by transfecting yeast with the mutagenized nucleic acids of SEQ ID NOS: 1, 3, 5, 7, 9 and 11 under suitable conditions such that the yeast display the T cell receptors on their surface. An anti-TCR antibody or other labeling reagent can then be used to identify, such as by flow cytometry, the yeast expressing suitable T cell receptor mutants on their surface. Conventional binding assays measuring the avidity of the mutant T cell receptors for the appropriate peptide/ Major Histocompatibility Complexes can be used to select desired derivatives of nucleic acids of SEQ ID NOS: 1, 3, 5, 7, 9, and 11. Further guidance can be obtained from Kieke et al., *Proc. Natl. Acad. Sci.* (*USA*) 96:5651-5656 (1999) and Holler et al., *Proc. Natl. Acad. Sci.* (*USA*) 96:5387-5392 (2000).

The invention also provides nucleic acids mutated in the nucleic acids encoding variants of SEQ ID NO: 2, 4, 6, 8, 10, or 12 in which the CDR3 regions of the these proteins has been mutated by addition, deletion, and/or mutation, but preferably mutation, of one, two, three, three to five, three to ten, five to ten, five to twenty, or ten to twenty amino acids of the CDR3 regions. The variant α- and β-chains produced thereby preferably have the functions of variant TCRs described previously herein.

The nucleic acids encoding the α- and β-chains of the invention can be further optimized by replacing codons yielding low levels of translation with codons yielding high levels of translation. Suitable examples of codon optimization in the art are provided by Frelin et al., *Gene Therapy* 11:522-533 (2004), Disbrow et al., *Virology* 311:105-114 (2003), Gao et al. *Biotechnol. Prog.* 20:443-448 (2004) and Ramakrishna et al., *Journal of Virology* 78:9174-9189 (2004)/

The nucleic acids of the invention described herein are preferably operably linked to a suitable promoter, which is preferably functional in T cells. Viral promoters, such as, without limitation, the major late CMV promoter, the RSV promoter, and the promoter found in the long-terminal repeat of the murine stem cell virus are among the preferred promoters useful in the context of the invention. Additional suitable genetic elements known in the art can also be ligated to, attached to, or inserted into the inventive nucleic acid and constructs to provide additional functions, level of expression, or pattern of expression. The native promoters for expression of these TCR genes can also be used provided that they are not used in the chromosome naturally encoding them unless modified by a process that substantially changes the chromosome. Such substantially changed chromosomes can include chromosomes transfected and altered by a retroviral vector or similar process.

The nucleic acids described above can be inserted into any suitable vector. Suitable vectors include without limitation viral vectors. Suitable viral vectors include without limitation retroviral vectors, alphaviral, vaccinia, adenoviral, adenoassociated viral, herpes viral, and fowl pox viral vectors, and preferably have a native or engineered capacity to transfect T cells. Additionally, the vectors useful in the context of the invention can be "naked" nucleic acid vectors (i.e., vectors having little or no proteins, sugars, and/or lipids encapsulating them), or complexed with other molecules. Other molecules that can be suitably combined with the inventive nucleic acids include without limitation viral coats, cationic lipids, liposomes, and targeting moieties such as ligands or receptors for target cell surface molecules.

A preferred vector provided by the invention comprises a portion of the murine stem cell virus LTR or a known analog thereof. Vectors further comprising the gag region and env splice site, which is preferably obtained from the vector SFGtcLuc+ITE4-(which is known in the art), are more preferred.

In another embodiment, the vector of the invention contains a single chain TCR encoding both α-chain and β-chain specific sequences in a single polypeptide. When the vector comprises a single chain TCR, it can, but preferably does not contain other TCR-related polypeptides. It is convenient, however, to incorporate nucleic acids encoding portions of the α-chain and β-chain of a single TCR (or variant thereof) into a single vector, in which event each of the two nucleic acids independently can be in any of the six reading frames, and positioned proximally or distally to each other. When the two nucleic acids are placed proximal to each other in a vector it is often-convenient to drive the expression of both nucleic acids from a single promoter and to include an internal ribosome binding site (IRES) 5' of the second nucleic acid. Alternatively, a second promoter, such as a phosphoglycerol kinase (PGK) promoter (Morgan et al., *J. Immunol.*, 171, 3287-3295 (2003)) can be used to drive the expression of the second nucleic acid construct.

In another embodiment, a "single-chain" TCR construct in which portions of SEQ ID NOS: 2 and 4, or SEQ ID NOS: 6 and 8, or SEQ ID NOS: 10 and 12, can be encoded by a nucleic acid encoding a single polypeptide. Methods of making such scTCRs are now conventional in the art, and produce a single polypeptide with the ability to recognize a suitable tumor antigen in the context of a suitable MHC. Such scTCRs are preferably soluble in aqueous solutions or blood or both, and can be conjugated to a detection moiety such as a fluor, an epitope for a labeled antibody, an enzyme (e.g., an enzyme capable of causing a colorimetric or luminescent reaction, such as horse radish peroxidase), or a nucleic acid, or one of many other detection moieties known in the art.

The nucleic acids of the invention can be introduced into any suitable source of cells, desirably any suitable source of T cells. For example, suitable T cells can be obtained from tumors (including, i.e., tumor infiltrating lymphocytes (TIL), peripheral blood (e.g., PBL), or lymph or lymph nodes, or any other suitable source.

The nucleic acids and vectors of the invention can be transduced into cells either in vitro or in vivo. The invention is not dependent on any particular means of transduction. Suitable means are well known to those skilled in the art, and continue to be further developed. Suitable means include without limitation electroporation, transformation, transduction, conjugation or triparental mating, cotransfection, coinfection, membrane fusion (especially with cationic lipids), liposome-cell fusion, high velocity bombardment with nucleic acid-coated or vector-coated microprojectiles, incubation with calcium phosphate-DNA precipitate, direct microinjection into single cells, and the like. Other methods also are available and are known to those skilled in the art.

Suitable methods of administering a vector of the invention to a mammal for purposes of gene therapy are known (see, e.g., Rosenfeld et al., *Science,* 252, 431-434 (1991); Jaffe et al., *Clin. Res.,* 39, 302A (1991); Rosenfeld et al., *Clin. Res.,* 39, 311A (1991); Berkner, *BioTechniques,* 6, 616-629 (1988); Crystal et al., *Human Gene Ther.,* 6, 643-666 (1995); Crystal et al., *Human Gene Ther.,* 6, 667-703 (1995)). T cells can be found in most locations in the mammalian body. Accordingly, any suitable route of administration can be used. Intravenous administration of cells is preferred when the mammal is human. A particular route can provide a more immediate and more effective reaction than another route. Pharmaceutically acceptable excipients also are well-known to those who are skilled in the art, and are readily available. The choice of excipient will be determined in part by the particular method used to administer the recombinant vector. Accordingly, there is a wide variety of suitable formulations for use in the context of the invention.

Moreover, to optimize the ability of vectors, and particularly viral vectors, to enter the cell by the method of the invention, preferably the method is carried out in the absence of neutralizing antibodies directed against the particular vector being introduced intracellularly, which could impede transduction of target cells. The ordinarily skilled artisan can routinely test for the presence of such neutralizing antibodies. Techniques are also known in the art to prevent the presence of neutralizing antibodies from impeding effective protein production (see, e.g., International Patent Application WO 96/12406).

The following methods, formulations, and excipients for administering the inventive nucleic acids, vectors, and cells are merely exemplary and are in no way limiting.

Formulations suitable for oral administration of the nucleic acids and vectors can consist of (a) liquid solutions, such as an effective amount of the compound dissolved in diluents, such as water, saline, or orange juice; (b) suspensions in an appropriate liquid; and (c) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients.

Preferred formulations include aqueous and non-aqueous, isotonic sterile injection solutions, which can contain antioxidants, buffers, bacteriostats, and solutes that render the formulation isotonic with blood, and aqueous and non-aqueous sterile suspensions that can include suspending agents, solubilizers, thickening agents, stabilizers, and preservatives. The inventive nucleic acids and vectors can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The nucleic acids, vectors and cells of the invention can be formulated in unit-dose or multi-dose sealed containers, such as ampules and vials, and can be stored frozen. These nucleic acids, vectors and cells of the invention can be stored in light-resistant packaging, employing for example, colored glass vials or cardboard boxes. Similarly, instructions for use of the compositions, which preferably comply with the regulations of the U.S. Food and Drug Administration, and more preferably also with its European and Japanese equivalent agencies, can be included with these compositions. These nucleic acids, vectors and cells of the invention are preferably also free from non-recombinant microbes (including without limitation fungi and mycobacteria) and non-recombinant viruses. Preferably, the instructions suggest the use a certain quantity of one of these compositions (or range of quantities), or suggest administration of the composition to a mammal for research or therapy via a particular route of administration.

Additionally, a cell, and more preferably, a nucleic acid or vector of the invention can be made into suppositories by mixing with a variety of bases such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The dose administered to an animal, particularly a human, in the context of the invention will vary with the inventive embodiment, the composition employed, the method of administration, and the particular site and organism being treated. However, the dose should be sufficient to provide a therapeutic response.

Any suitable number of transduced T cells can be administered to a mammal. While a single T cell is capable of expanding and providing a benefit, it is preferable to administer at least $10^3$, more preferably at least $10^5$, even more preferably at least $10^8$ and optionally $10^{12}$ or more transduced T cells. One preferred embodiment of the invention comprises administration of from about $10^8$ to about $10^{12}$ transduced T cells to a human. There is no theoretical upper limit on the number of transduced T cells that can be administered to a mammal or the number of times that T cells can be administered to a mammal. The ordinarily skilled artisan will appreciate, however, that the excessive quantities of administered T cells (e.g., in some embodiments more than $10^{15}$ or $10^{18}$ transduced cells) can exceed the mammal's ability to support them, lead to undesirable clinical sequelae, and unnecessarily increase costs. Similarly, excessive administrations of therapeutic compositions to mammals can lead to undesirable effects such as allergic responses and infection, and so are preferably avoided.

A composition comprising transduced T cells can be prepared so that it does not contain living cells other than blood cells and lymphocytes. That is, the composition can be sterile except for the transduced blood cells, lymphocytes, or T cells. Such compositions can be readily prepared by positive and negative selection of the desired cells from a population of cells transduced with the inventive nucleic acids or vectors. Suitable positive selection techniques include bioaffinity separations, which are well known in the art. For example, an antibody specific for a cell surface antigen of a T cell can be linked to a magnetic bead, incubated with the transduced population, separated therefrom and optionally washed. Similarly, undesired cells can be eliminated from the composition by any suitable technique. Suitable negative selection techniques include immunomagnetic removal of undesired cells, and the use of antibiotics to destroy microbes. Moreover, leukophoresis, other filtration techniques, sterile technique, differential centrifugation, and other conventional methods can be used to produce a composition suitable for administration to a human.

In embodiments in which the mammal is subjected to lymphodepletion and cytokine or growth factor stimulation, any suitable regimen can be used. Dudley et al., *Science*, 298, 850-854 (2002) and the supporting online materials available from the journal or at www.sciencemag.org/cgi/content/full/1076514/DC1 (10.1126/science.1076514), Rosenberg et al., *J. Natl. Cancer Inst.*, 86, 1159-1166 (1994) and Dudley et al., *J. Immunother.*, 25, 243-251 (2002), as well as other references described in these references, discuss one suitable lymphodepletion and IL-2 stimulation regimen. These references suggest, for example, treatment of a human with 7 days of immunodepleting doses of cyclophosphamide (about 60 mg/kg) and fludarabine (about 25 mg/m$^2$) and high-doses of IL-2 (about 720,000 IU/kg). Administration of IL-2 is preferably repeated multiple times and more preferably repeated 3 to 15 times, and is preferably, administered 1-5 times daily, which numbers can be selected and adjusted within the discretion of the skilled medical artisan.

The following examples further illustrate the invention but, of course, should not be construed as limiting its scope.

EXAMPLE 1

This example shows that transfer of nucleic acids encoding SEQ ID NOS: 10 and 12 (i.e., an α- and β-chain of the highly avid anti-gp100 TCR disclosed herein) to a bulk population of peripheral blood lymphocytes (PBL) causes the PBL to acquire specificity for cancer cells expressing gp100 and to destroy such cancer cells.

Poly(A)+ RNA was isolated from R6C12 cells, which are high avidity CTL clones derived from a melanoma patient that was vaccinated with gp100 peptide (gp100:209-217 (210M)). RT-PCR was performed using oligonucleotides disclosed in Morgan et al., *J. Immunol.*, 171, 3288 (2003). The individual PCR products were inserted into the pCR2.1 vector using the TA cloning method. The β-chains were combined with the phosphoglycerol kinase promoter or an IRES. PG13 gibbon ape leukemia virus-packaging cells and the human ecotropic packaging cell line, Phoenix Eco, were co-cultured and transformed with the constructs. After 14 days of co-culture, the Phoenix Eco cells were removed from the culture by negative selection with magnetic beads conjugated with anti-LYT-2 antibodies. The clones were expanded and high titer clones were selected by dot-blot titration. Southern blotting was performed to confirm vector integration and copy number.

PBL were collected by leukophoresis, and lymphocytes were separated by centrifugation on a Ficoll/Hypaque cushion, washed in HBSS, then resuspended at a concentration of 1×10$^6$/ml in AIM-V medium supplemented with ng/ml OKT3, 300 IU/ml IL-2, and 5% human AB serum. The lymphocytes were cultured in vitro for 48 hours before transduction. Following stimulation, lymphocytes were transduced with retroviral vectors by transfer to culture dishes that had been precoated with retroviral vectors. To coat culture plates with vector, nontissue culture-treated six-well plates were first treated with 25 μg/ml recombinant fibronectin fragment (RetroNectin™, Takara, Otsu, Japan). To these plates was then added retroviral vector supernatant, and the plates were incubated at 32° C., and the procedure was repeated the following day, after which time cells were expanded at 37° C. in a 5% CO$_2$ incubator and split as necessary to maintain cell density between 0.5×10$^6$ cells/ml and 4×10$^6$ cells/ml.

To determine melanoma reactivity, two HLA-A2-positive melanoma cell lines and two non-HLA-A2 melanoma cell lines were co-cultured with TCR and control vector transduced PBL cultures from a melanoma patient. HLA-A2 restricted IFN-γ release (in the range of 866-2528 pg/ml) was demonstrated with two PBL populations transduced with different vectors, with no specific production of IFN-γ observed in co-culture of HLA-A2-negative cells expressing gp-100 (as a negative control). The retrovirally-transduced cells expressing SEQ ID NOS: 10 and 12 also were able to specifically release GM-CSF and TNF-α.

In a chromium release assay, the inventive cells readily lysed HLA-A2 melanoma lines, without causing substantial damage to non-HLA-A2 cell lines. Additionally, mock and control-vector transduced cells were non-reactive with the target cells. Finally, the modified T cells expressing SEQ ID NOS: 10 and 12 reacted with cognate targets similarly to CTL clones.

Accordingly, this example shows that transduction of PBL with an nucleic acid encoding SEQ ID NOS: 10 and 12 produces a population of T cells that appropriately secrete cytokines when contacted to appropriate target cells, and effectively lyse cognate target cells.

EXAMPLE 2

This example demonstrates that TIL can be used in accordance with the invention as well as PBL. TIL are T lymphocytes already possessing an anti-tumor activity. Use of the inventive method with TIL can enhance their anti-cancer properties.

Three non-reactive cultures of TIL were transduced with a vector encoding SEQ ID NOS: 10 and 12 and cultured. Each cultured transduced TIL produced IFN-γ, GM-CSF, and TNF-α in response to gp100 peptide-pulsed T2 cells, Which has a sequence of either ITDQVPFSV (SEQ ID NO:17) or IMDQVPFSV (SEQ ID NO:18), whereas control-transduced cells remained non-reactive. Autologous tumor reactivity was also assessed and did not appear to be affected by transduction with the vector encoding SEQ ID NOS: 10 and 12.

Thus, this example demonstrates that TIL are a suitable source of T cells in the context of the invention.

EXAMPLE 3

This example shows that CD4$^+$ cells can also be effectively transduced with a vector encoding SEQ ID NOS: 10 and 12 to provide a useful modified T cell.

PBL were transduced with a vector encoding SEQ ID NOS: 10 and 12, and the CD8$^+$ population was reduced to 0.3%. This population consisting essentially of CD4+ cells produced 10-fold more cytokines when contacted to gp100- pulsed T2 cells (expressing HLA-A2), and three fold more cytokines than a 1% CD8+ population of PBL transduced with this vector.

Accordingly, this example shows that CD4+ cells can be usefully transduced in accordance with the invention.

EXAMPLE 4

This example shows that transfer of nucleic acids encoding SEQ ID NOS: 2 and 4 (i.e., an α- and β-chain of the highly avid anti-MART-1 TCR disclosed herein) to a bulk population of peripheral blood lymphocytes (PBL) causes the PBL to acquire specificity for cancer cells expressing MART-1 and to destroy these cancer cells.

Nucleic acids encoding SEQ ID NOS: 2 and 4 were isolated from T lymphocytes that mediated in vivo regression of a tumor in a patient with metastatic melanoma. These genes were cloned and inserted into MSCV-based retroviral vectors. cDNAs encoding SEQ ID NOS: 2 and 4 were cloned into a vector comprising a murine stem cell virus long terminal repeat, and a PGK-IRES-NEO cassette substitutionally inserted into the SPeI-XhoI sites of the extended gag region and env splice site from SFGtcLuc+ITE4 (Lindemann et al., *Mol. Med.*, 3, 466-476 (1997)) of pMINV (Hawley et al., *Ann. NY Acad. Sci.*, 795, 341-345 (1996)). The vectors were also modified to contain a naturally-occurring Kozak sequence taken from the vector GCsap (Onodera et al., *J. Virol.*, 72, 1769-1774 (1998)) using the PmlI-XhoI sites. Three vectors so produced are discussed below: Vector AIB contains a DNA encoding SEQ ID NO: 2 followed by an IRES followed by a DNA encoding SEQ ID NO: 4; vector BIA is the same as vector AIB except that the nucleic acids encoding SEQ ID NOS: 2 and 4 are juxtaposed, and the vector BPA contains a DNA encoding SEQ ID NO: 4, followed by a PGK promoter, followed by DNA encoding SEQ ID NO: 2. A fourth similar vector failed to effectively transduce a comparable number of cells as the three discussed previously, and so was not used further.

T cells were transduced with these vectors according to the method of Example 1. These transduced cells, when contacted to appropriate target cells, secreted quantities of IFN-γ, GM-CSF, IL-2, and TNF-α that were similar and often greater than the quantities secreted from a positive control CTL clone, and significantly greater than that secreted from appropriate negative control cells (although the quantity of IL-2 produced both by the transduced T cells and the positive control was not high). Significantly, the transduced PBL recognized T2 cells pulsed with as little as 0.1 ng/ml of MART-1 peptide, which has a sequence of EAAGIGILTL (SEQ ID NO:19) or ELAGIGILTL (SEQ ID NO:20).

Moreover, PBL transduced by the AIB vector readily lysed HLA A2+ melanoma cell lines, but not HLA A2− cell lines, and mock transduced PBL did not cause lysis of the target cells used in a chromium-release experiment.

Additionally, transduced populations of TIL also were stimulated to release appropriate levels of cytokines in response to appropriate target cells.

Also, transduced PBL were stimulated with an appropriate antigen, and, in the absence of exogenous IL-2, more than 12.5% of the transduced cells (i.e., 25% of the transduced cells) divided compared to 2-5% of control cells. Similarly, in the presence of minimal amounts of IL-2, up to 55% of the transduced cells divided, whereas only 7-13% of control cultures proliferated.

EXAMPLE 5

This example shows that transfer of nucleic acids encoding SEQ ID NOS: 6 and 8 (i.e., an α- and β-chain of the highly avid anti-NY-ESO-1 TCR disclosed herein) to a bulk population of peripheral blood lymphocytes (PBL) causes the PBL to acquire specificity for cancer cells expressing MART-1 and to destroy these cancer cells.

Nucleic acids encoding SEQ ID NOS: 6 and 8 were cloned into a retroviral vector comprising a murine stem cell virus promoter and used to generate a high titer packaging cell lines in a manner similar to that used in the preceding examples. Peptides used to test the anti-NY-ESO-1 TCR included NY-ESO-1 p157-165 (SLLMWTTQC) (SEQ ID NO: 13), NY-ESO-1 p157-165V (SLLMWTTQV) (SEQ ID NO: 14), NY-ESO-1 p157-168 (SLLMWTTQCFLP) (SEQ ID NO: 15), NY-ESO-1 p161-180 (WITQCFLPVFLAQPPSGQRA) (SEQ ID NO: 16), an HLA-DP4 restricted epitope) gp100 209-217, and MART-1 27-35.

Transduced lymphocytes efficiently recognized and killed T2 cells having HLA-A2 and presenting NY-ESO-1 peptide. Chromium release assays demonstrated that as little as 20 pM NY-ESO-1 peptide was required to stimulate killing in vitro. Transduced CD4+ T cells co-cultured with NY-ESO-1 peptide pulsed T2 cells produced IFN-γ, GM-CSF, IL-4, and IL-10, which reasonably suggests that the CD8-independent activation of these cells. Additionally, transduced T cells efficiently recognized NY-ESO-1 positive non-melanoma tumor cell lines.

Accordingly, this example shows that T cells can be usefully transduced with nucleic acids encoding SEQ ID NOS: 6 and 8, and also that these transduced T cells should reasonably be expected to treat cancer in a patient in need thereof.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated nucleic acid molecule encoding an amino acid sequence selected from the group consisting of SEQ ID NO: 2 and SEQ ID NO: 4, and wherein said nucleic acid molecule encodes a chain of a T cell receptor (TCR) which binds a tumor antigen in the context of a major histocompatibility complex (MHC).

2. The isolated nucleic acid molecule of claim 1 wherein the nucleic acid molecule encodes the alpha (α) chain of a TCR that recognizes a tumor antigen.

3. The isolated nucleic acid molecule of claim 1, wherein the nucleic acid molecule encodes the beta (β) chain of a TCR that recognizes a tumor antigen.

4. The isolated nucleic acid molecule of claim 1, wherein the nucleic acid molecule comprises a sequence consisting essentially of SEQ ID NO: 1 or SEQ ID NO: 3.

5. A vector comprising the isolated nucleic acid molecule of claim 1.

6. The vector of claim 5, wherein the vector is a viral vector.

7. The vector of claim 6, wherein the viral vector is a retroviral vector.

8. A composition comprising the isolated nucleic acid molecule of claim 1, wherein the nucleic acid molecule optionally is inserted into a vector, and a pharmaceutically acceptable carrier.

9. An isolated nucleic acid molecule encoding a polypeptide comprising the variable and hypervariable portions of SEQ ID NO: 2 and SEQ ID NO: 4, wherein the polypeptide recognizes a MART-1 peptide in the context of an MHC.

10. A method of making a tumor-reactive T lymphocyte, comprising transducing a T lymphocyte with a nucleic acid molecule encoding SEQ ID NO: 2 and SEQ ID NO: 4, wherein the nucleic acid molecule is inserted into a vector.

11. The nucleic acid molecule of claim 1, wherein the tumor antigen is MART-1.

* * * * *

SEQUENCE LISTING

```
<160> NUMBER OF SEQ ID NOS: 20

<210> SEQ ID NO 1
<211> LENGTH: 807
<212> TYPE: DNA
<213> ORGANISM: Homo sapiens
<220> FEATURE:
<221> NAME/KEY: CDS
<222> LOCATION: (1)..(807)

<400> SEQUENCE: 1 atg ttg ctt gaa cat tta tta ata atc ttg tgg atg cag ctg aca tgg      48
Met Leu Leu Glu His Leu Leu Ile Ile Leu Trp Met Gln Leu Thr Trp
1               5                   10                  15 gtc agt ggt caa cag ctg aat cag agt cct caa tct atg ttt atc cag      96
Val Ser Gly Gln Gln Leu Asn Gln Ser Pro Gln Ser Met Phe Ile Gln
                20                  25                  30 gaa gga gaa gat gtc tcc atg aac tgc act tct tca agc ata ttt aac      144
Glu Gly Glu Asp Val Ser Met Asn Cys Thr Ser Ser Ser Ile Phe Asn
            35                  40                  45 acc tgg cta tgg tac aag cag gac cct ggg gaa ggt cct gtc ctc ttg      192
Thr Trp Leu Trp Tyr Lys Gln Asp Pro Gly Glu Gly Pro Val Leu Leu
        50                  55                  60 ata gcc tta tat aag gct ggt gaa ttg acc tca aat gga aga ctg act      240
Ile Ala Leu Tyr Lys Ala Gly Glu Leu Thr Ser Asn Gly Arg Leu Thr
65                  70                  75                  80 gct cag ttt ggt ata acc aga aag gac agc ttc ctg aat atc tca gca      288
Ala Gln Phe Gly Ile Thr Arg Lys Asp Ser Phe Leu Asn Ile Ser Ala
                85                  90                  95 tcc ata cct agt gat gta ggc atc tac ttc tgt gct ggt ggg acc ggt      336
Ser Ile Pro Ser Asp Val Gly Ile Tyr Phe Cys Ala Gly Gly Thr Gly
                100                 105                 110 aac cag ttc tat ttt ggg aca ggg aca agt ttg acg gtc att cca aat      384
Asn Gln Phe Tyr Phe Gly Thr Gly Thr Ser Leu Thr Val Ile Pro Asn
            115                 120                 125 atc cag aac cct gac cct gcc gtg tac cag ctg aga gac tct aaa tcc      432
Ile Gln Asn Pro Asp Pro Ala Val Tyr Gln Leu Arg Asp Ser Lys Ser
        130                 135                 140 agt gac aag tct gtc tgc cta ttc acc gat ttt gat tct caa aca aat      480
Ser Asp Lys Ser Val Cys Leu Phe Thr Asp Phe Asp Ser Gln Thr Asn
145                 150                 155                 160 gtg tca caa agt aag gat tct gat gtg tat atc aca gac aaa act gtg      528
Val Ser Gln Ser Lys Asp Ser Asp Val Tyr Ile Thr Asp Lys Thr Val
                165                 170                 175 cta gac atg agg tct atg gac ttc aag agc aac agt gct gtg gcc tgg      576
Leu Asp Met Arg Ser Met Asp Phe Lys Ser Asn Ser Ala Val Ala Trp
            180                 185                 190 agc aac aaa tct gac ttt gca tgt gca aac gcc ttc aac aac agc att      624
Ser Asn Lys Ser Asp Phe Ala Cys Ala Asn Ala Phe Asn Asn Ser Ile
        195                 200                 205 att cca gaa gac acc ttc ttc ccc agc cca gaa agt tcc tgt gat gtc      672
Ile Pro Glu Asp Thr Phe Phe Pro Ser Pro Glu Ser Ser Cys Asp Val
    210                 215                 220 aag ctg gtc gag aaa agc ttt gaa aca gat acg aac cta aac ttt caa      720
Lys Leu Val Glu Lys Ser Phe Glu Thr Asp Thr Asn Leu Asn Phe Gln
225                 230                 235                 240 aac ctg tca gtg att ggg ttc cga atc ctc ctc ctg aag gtg gcc ggg      768
Asn Leu Ser Val Ile Gly Phe Arg Ile Leu Leu Leu Lys Val Ala Gly
```

```
                        245                 250                 255
ttt aat ctg ctc atg acg ctg cgg ctg tgg tcc agc tga                       807
Phe Asn Leu Leu Met Thr Leu Arg Leu Trp Ser Ser
            260                 265

<210> SEQ ID NO 2
<211> LENGTH: 268
<212> TYPE: PRT
<213> ORGANISM: Homo sapiens

<400> SEQUENCE: 2

Met Leu Leu Glu His Leu Leu Ile Ile Leu Trp Met Gln Leu Thr Trp
1               5                   10                  15

Val Ser Gly Gln Gln Leu Asn Gln Ser Pro Gln Ser Met Phe Ile Gln
            20                  25                  30

Glu Gly Glu Asp Val Ser Met Asn Cys Thr Ser Ser Ile Phe Asn
        35                  40                  45

Thr Trp Leu Trp Tyr Lys Gln Asp Pro Gly Glu Gly Pro Val Leu Leu
    50                  55                  60

Ile Ala Leu Tyr Lys Ala Gly Glu Leu Thr Ser Asn Gly Arg Leu Thr
65                  70                  75                  80

Ala Gln Phe Gly Ile Thr Arg Lys Asp Ser Phe Leu Asn Ile Ser Ala
                85                  90                  95

Ser Ile Pro Ser Asp Val Gly Ile Tyr Phe Cys Ala Gly Gly Thr Gly
            100                 105                 110

Asn Gln Phe Tyr Phe Gly Thr Gly Thr Ser Leu Thr Val Ile Pro Asn
        115                 120                 125

Ile Gln Asn Pro Asp Pro Ala Val Tyr Gln Leu Arg Asp Ser Lys Ser
    130                 135                 140

Ser Asp Lys Ser Val Cys Leu Phe Thr Asp Phe Asp Ser Gln Thr Asn
145                 150                 155                 160

Val Ser Gln Ser Lys Asp Ser Asp Val Tyr Ile Thr Asp Lys Thr Val
                165                 170                 175

Leu Asp Met Arg Ser Met Asp Phe Lys Ser Asn Ser Ala Val Ala Trp
            180                 185                 190

Ser Asn Lys Ser Asp Phe Ala Cys Ala Asn Ala Phe Asn Asn Ser Ile
        195                 200                 205

Ile Pro Glu Asp Thr Phe Phe Pro Ser Pro Glu Ser Ser Cys Asp Val
    210                 215                 220

Lys Leu Val Glu Lys Ser Phe Glu Thr Asp Thr Asn Leu Asn Phe Gln
225                 230                 235                 240

Asn Leu Ser Val Ile Gly Phe Arg Ile Leu Leu Leu Lys Val Ala Gly
                245                 250                 255

Phe Asn Leu Leu Met Thr Leu Arg Leu Trp Ser Ser
            260                 265

<210> SEQ ID NO 3
<211> LENGTH: 930
<212> TYPE: DNA
<213> ORGANISM: Homo sapiens
<220> FEATURE:
<221> NAME/KEY: CDS
<222> LOCATION: (1)..(930)

<400> SEQUENCE: 3 atg ggc aca agg ttg ttc ttc tat gtg gcc ctt tgt ctc ctg tgg aca        48
Met Gly Thr Arg Leu Phe Phe Tyr Val Ala Leu Cys Leu Leu Trp Thr
1               5                   10                  15
```

```
gga cac atg gat gct gga atc acc cag agc cca aga cac aag gtc aca      96
Gly His Met Asp Ala Gly Ile Thr Gln Ser Pro Arg His Lys Val Thr
         20                  25                  30 gag aca gga aca cca gtg act ctg aga tgt cac cag act gag aac cac     144
Glu Thr Gly Thr Pro Val Thr Leu Arg Cys His Gln Thr Glu Asn His
             35                  40                  45 cgc tat atg tac tgg tat cga caa gac ccg ggg cat ggg ctg agg ctg     192
Arg Tyr Met Tyr Trp Tyr Arg Gln Asp Pro Gly His Gly Leu Arg Leu
 50                  55                  60 atc cat tac tca tat ggt gtt aaa gat act gac aaa gga gaa gtc tca     240
Ile His Tyr Ser Tyr Gly Val Lys Asp Thr Asp Lys Gly Glu Val Ser
 65                  70                  75                  80 gat ggc tat agt gtc tct aga tca aag aca gag gat ttc ctc ctc act     288
Asp Gly Tyr Ser Val Ser Arg Ser Lys Thr Glu Asp Phe Leu Leu Thr
                 85                  90                  95 ctg gag tcc gct acc agc tcc cag aca tct gtg tac ttc tgt gcc atc     336
Leu Glu Ser Ala Thr Ser Ser Gln Thr Ser Val Tyr Phe Cys Ala Ile
            100                 105                 110 agt gag gta ggg gtt ggg cag ccc cag cat ttt ggt gat ggg act cga     384
Ser Glu Val Gly Val Gly Gln Pro Gln His Phe Gly Asp Gly Thr Arg
            115                 120                 125 ctc tcc atc cta gag gac ctg aac aag gtg ttc cca ccc gag gtc gct     432
Leu Ser Ile Leu Glu Asp Leu Asn Lys Val Phe Pro Pro Glu Val Ala
130                 135                 140 gtg ttt gag cca tca gaa gca gag atc tcc cac acc caa aag gcc aca     480
Val Phe Glu Pro Ser Glu Ala Glu Ile Ser His Thr Gln Lys Ala Thr
145                 150                 155                 160 ctg gtg tgc ctg gcc aca ggc ttc ttc cct gac cac gtg gag ctg agc     528
Leu Val Cys Leu Ala Thr Gly Phe Phe Pro Asp His Val Glu Leu Ser
                165                 170                 175 tgg tgg gtg aat ggg aag gag gtg cac agt ggg gtc agc acg gac ccg     576
Trp Trp Val Asn Gly Lys Glu Val His Ser Gly Val Ser Thr Asp Pro
            180                 185                 190 cag ccc ctc aag gag cag ccc gcc ctc aat gac tcc aga tac tgc ctg     624
Gln Pro Leu Lys Glu Gln Pro Ala Leu Asn Asp Ser Arg Tyr Cys Leu
            195                 200                 205 agc agc cgc ctg agg gtc tcg gcc acc ttc tgg cag aac ccc cgc aac     672
Ser Ser Arg Leu Arg Val Ser Ala Thr Phe Trp Gln Asn Pro Arg Asn
210                 215                 220 cac ttc cgc tgt caa gtc cag ttc tac ggg ctc tcg gag aat gac gag     720
His Phe Arg Cys Gln Val Gln Phe Tyr Gly Leu Ser Glu Asn Asp Glu
225                 230                 235                 240 tgg acc cag gat agg gcc aaa ccc gtc acc cag atc gtc agc gcc gag     768
Trp Thr Gln Asp Arg Ala Lys Pro Val Thr Gln Ile Val Ser Ala Glu
                245                 250                 255 gcc tgg ggt aga gca gac tgt ggc ttt acc tcg gtg tcc tac cag caa     816
Ala Trp Gly Arg Ala Asp Cys Gly Phe Thr Ser Val Ser Tyr Gln Gln
            260                 265                 270 ggg gtc ctg tct gcc acc atc ctc tat gag atc ctg cta ggg aag gcc     864
Gly Val Leu Ser Ala Thr Ile Leu Tyr Glu Ile Leu Leu Gly Lys Ala
            275                 280                 285 acc ctg tat gct gtg ctg gtc agc gcc ctt gtg ttg atg gcc atg gtc     912
Thr Leu Tyr Ala Val Leu Val Ser Ala Leu Val Leu Met Ala Met Val
            290                 295                 300 aag aga aag gat ttc tga                                             930
Lys Arg Lys Asp Phe
305

<210> SEQ ID NO 4
<211> LENGTH: 309
<212> TYPE: PRT
```

<213> ORGANISM: Homo sapiens

<400> SEQUENCE: 4

```
Met Gly Thr Arg Leu Phe Phe Tyr Val Ala Leu Cys Leu Leu Trp Thr
1               5                   10                  15
Gly His Met Asp Ala Gly Ile Thr Gln Ser Pro Arg His Lys Val Thr
            20                  25                  30
Glu Thr Gly Thr Pro Val Thr Leu Arg Cys His Gln Thr Glu Asn His
        35                  40                  45
Arg Tyr Met Tyr Trp Tyr Arg Gln Asp Pro Gly His Gly Leu Arg Leu
    50                  55                  60
Ile His Tyr Ser Tyr Gly Val Lys Asp Thr Asp Lys Gly Glu Val Ser
65                  70                  75                  80
Asp Gly Tyr Ser Val Ser Arg Ser Lys Thr Glu Asp Phe Leu Leu Thr
                85                  90                  95
Leu Glu Ser Ala Thr Ser Ser Gln Thr Ser Val Tyr Phe Cys Ala Ile
            100                 105                 110
Ser Glu Val Gly Val Gly Gln Pro Gln His Phe Gly Asp Gly Thr Arg
        115                 120                 125
Leu Ser Ile Leu Glu Asp Leu Asn Lys Val Phe Pro Pro Glu Val Ala
    130                 135                 140
Val Phe Glu Pro Ser Glu Ala Glu Ile Ser His Thr Gln Lys Ala Thr
145                 150                 155                 160
Leu Val Cys Leu Ala Thr Gly Phe Phe Pro Asp His Val Glu Leu Ser
                165                 170                 175
Trp Trp Val Asn Gly Lys Glu Val His Ser Gly Val Ser Thr Asp Pro
            180                 185                 190
Gln Pro Leu Lys Glu Gln Pro Ala Leu Asn Asp Ser Arg Tyr Cys Leu
        195                 200                 205
Ser Ser Arg Leu Arg Val Ser Ala Thr Phe Trp Gln Asn Pro Arg Asn
    210                 215                 220
His Phe Arg Cys Gln Val Gln Phe Tyr Gly Leu Ser Glu Asn Asp Glu
225                 230                 235                 240
Trp Thr Gln Asp Arg Ala Lys Pro Val Thr Gln Ile Val Ser Ala Glu
                245                 250                 255
Ala Trp Gly Arg Ala Asp Cys Gly Phe Thr Ser Val Ser Tyr Gln Gln
            260                 265                 270
Gly Val Leu Ser Ala Thr Ile Leu Tyr Glu Ile Leu Leu Gly Lys Ala
        275                 280                 285
Thr Leu Tyr Ala Val Leu Val Ser Ala Leu Val Leu Met Ala Met Val
    290                 295                 300
Lys Arg Lys Asp Phe
305
```

<210> SEQ ID NO 5
<211> LENGTH: 813
<212> TYPE: DNA
<213> ORGANISM: Homo sapiens
<220> FEATURE:
<221> NAME/KEY: CDS
<222> LOCATION: (1)..(813)

<400> SEQUENCE: 5

```
atg gaa act ctc ctg gga gtg tct ttg gtg att cta tgg ctt caa ctg      48
Met Glu Thr Leu Leu Gly Val Ser Leu Val Ile Leu Trp Leu Gln Leu
1               5                   10                  15 gct agg gtg aac agt caa cag gga gaa gag gat cct cag gcc ttg agc      96
```

```
                                      -continued

Ala Arg Val Asn Ser Gln Gln Gly Glu Glu Asp Pro Gln Ala Leu Ser
            20                  25                  30 atc cag gag ggt gaa aat gcc acc atg aac tgc agt tac aaa act agt        144
Ile Gln Glu Gly Glu Asn Ala Thr Met Asn Cys Ser Tyr Lys Thr Ser
         35                  40                  45 ata aac aat tta cag tgg tat aga caa aat tca ggt aga ggc ctt gtc        192
Ile Asn Asn Leu Gln Trp Tyr Arg Gln Asn Ser Gly Arg Gly Leu Val
 50                  55                  60 cac cta att tta ata cgt tca aat gaa aga gag aaa cac agt gga aga        240
His Leu Ile Leu Ile Arg Ser Asn Glu Arg Glu Lys His Ser Gly Arg
 65                  70                  75                  80 tta aga gtc acg ctt gac act tcc aag aaa agc agt tcc ttg ttg atc        288
Leu Arg Val Thr Leu Asp Thr Ser Lys Lys Ser Ser Ser Leu Leu Ile
                 85                  90                  95 acg gct tcc cgg gca gca gac act gct tct tac ttc tgt gct acg gac        336
Thr Ala Ser Arg Ala Ala Asp Thr Ala Ser Tyr Phe Cys Ala Thr Asp
             100                 105                 110 ggg gca ggc aaa tca acc ttt ggg gat ggg act acg ctc act gtg aag        384
Gly Ala Gly Lys Ser Thr Phe Gly Asp Gly Thr Thr Leu Thr Val Lys
         115                 120                 125 cca aat atc cag aag cct gac cct gcc gtg tac cag ctg aga gac tct        432
Pro Asn Ile Gln Lys Pro Asp Pro Ala Val Tyr Gln Leu Arg Asp Ser
130                 135                 140 aaa tcc agt gac aag tct gtc tgc cta ttc acc gat ttt gat tct caa        480
Lys Ser Ser Asp Lys Ser Val Cys Leu Phe Thr Asp Phe Asp Ser Gln
145                 150                 155                 160 aca aat gtg tca caa agt aag gat tct gat gtg tat atc aca gac aaa        528
Thr Asn Val Ser Gln Ser Lys Asp Ser Asp Val Tyr Ile Thr Asp Lys
                165                 170                 175 act gtg cta gac atg agg tct atg gac ttc aag agc aac agt gct gtg        576
Thr Val Leu Asp Met Arg Ser Met Asp Phe Lys Ser Asn Ser Ala Val
            180                 185                 190 gcc tgg agc aac aaa tct gac ttt gca tgt gca aac gcc ttc aac aac        624
Ala Trp Ser Asn Lys Ser Asp Phe Ala Cys Ala Asn Ala Phe Asn Asn
        195                 200                 205 agc att att cca gca gac acc ttc ttc ccc agc cca gaa agt tcc tgt        672
Ser Ile Ile Pro Ala Asp Thr Phe Phe Pro Ser Pro Glu Ser Ser Cys
210                 215                 220 gat gtc aag ctg gtc gag aaa agc ttt gaa aca gat acg aac cta aac        720
Asp Val Lys Leu Val Glu Lys Ser Phe Glu Thr Asp Thr Asn Leu Asn
225                 230                 235                 240 ttt caa aac ctg tca gtg att ggg ttc cga atc ctc ctc ctg aaa gtg        768
Phe Gln Asn Leu Ser Val Ile Gly Phe Arg Ile Leu Leu Leu Lys Val
                245                 250                 255 gcc ggg ttt aat ctg ctc atg acg ctg cgg ctg tgg tcc agc tga            813
Ala Gly Phe Asn Leu Leu Met Thr Leu Arg Leu Trp Ser Ser
            260                 265                 270

<210> SEQ ID NO 6
<211> LENGTH: 270
<212> TYPE: PRT
<213> ORGANISM: Homo sapiens

<400> SEQUENCE: 6

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45
```

```
Ile Asn Asn Leu Gln Trp Tyr Arg Gln Asn Ser Gly Arg Gly Leu Val
     50                  55                  60
His Leu Ile Leu Ile Arg Ser Asn Glu Arg Glu Lys His Ser Gly Arg
 65                  70                  75                  80
Leu Arg Val Thr Leu Asp Thr Ser Lys Lys Ser Ser Leu Leu Ile
                 85                  90                  95
Thr Ala Ser Arg Ala Ala Asp Thr Ala Ser Tyr Phe Cys Ala Thr Asp
                100                 105                 110
Gly Ala Gly Lys Ser Thr Phe Gly Asp Gly Thr Thr Leu Thr Val Lys
                115                 120                 125
Pro Asn Ile Gln Lys Pro Asp Pro Ala Val Tyr Gln Leu Arg Asp Ser
                130                 135                 140
Lys Ser Ser Asp Lys Ser Val Cys Leu Phe Thr Asp Phe Asp Ser Gln
145                 150                 155                 160
Thr Asn Val Ser Gln Ser Lys Asp Ser Asp Val Tyr Ile Thr Asp Lys
                165                 170                 175
Thr Val Leu Asp Met Arg Ser Met Asp Phe Lys Ser Asn Ser Ala Val
                180                 185                 190
Ala Trp Ser Asn Lys Ser Asp Phe Ala Cys Ala Asn Ala Phe Asn Asn
                195                 200                 205
Ser Ile Ile Pro Ala Asp Thr Phe Phe Pro Ser Pro Glu Ser Ser Cys
210                 215                 220
Asp Val Lys Leu Val Glu Lys Ser Phe Glu Thr Asp Thr Asn Leu Asn
225                 230                 235                 240
Phe Gln Asn Leu Ser Val Ile Gly Phe Arg Ile Leu Leu Leu Lys Val
                245                 250                 255
Ala Gly Phe Asn Leu Leu Met Thr Leu Arg Leu Trp Ser Ser
                260                 265                 270

<210> SEQ ID NO 7
<211> LENGTH: 927
<212> TYPE: DNA
<213> ORGANISM: Homo sapiens
<220> FEATURE:
<221> NAME/KEY: CDS
<222> LOCATION: (1)..(927)

<400> SEQUENCE: 7 atg gac tcc tgg acc ctc tgc tgt gtg tcc ctt tgc atc ctg gta gca      48
Met Asp Ser Trp Thr Leu Cys Cys Val Ser Leu Cys Ile Leu Val Ala
 1               5                  10                  15 aag cac aca gat gct gga gtt atc cag tca ccc cgg cac gag gtg aca      96
Lys His Thr Asp Ala Gly Val Ile Gln Ser Pro Arg His Glu Val Thr
                 20                  25                  30 gag atg gga caa gaa gtg act ctg aga tgt aaa cca att tca gga cac     144
Glu Met Gly Gln Glu Val Thr Leu Arg Cys Lys Pro Ile Ser Gly His
         35                  40                  45 gac tac ctt ttc tgg tac aga cag acc atg atg cgg gga ctg gag ttg     192
Asp Tyr Leu Phe Trp Tyr Arg Gln Thr Met Met Arg Gly Leu Glu Leu
 50                  55                  60 ctc att tac ttt aac aac aac gtt ccg ata gat gat tca ggg atg ccc     240
Leu Ile Tyr Phe Asn Asn Asn Val Pro Ile Asp Asp Ser Gly Met Pro
 65                  70                  75                  80 gag gat cga ttc tca gct aag atg cct aat gca tca ttc tcc act ctg     288
Glu Asp Arg Phe Ser Ala Lys Met Pro Asn Ala Ser Phe Ser Thr Leu
                 85                  90                  95 aag atc cag ccc tca gaa ccc agg gac tca gct gtg tac ttc tgt gcc     336
Lys Ile Gln Pro Ser Glu Pro Arg Asp Ser Ala Val Tyr Phe Cys Ala
                100                 105                 110
```

| | | | | | | | | | | | | | | | |
|---|---|---|---|---|---|---|---|---|---|---|---|---|---|---|---|
| agc | act | atc | ggg | gct | cag | ccc | cag | cat | ttt | ggt | gat | ggg | act | cga | ctc | 384 |
| Ser | Thr | Ile | Gly | Ala | Gln | Pro | Gln | His | Phe | Gly | Asp | Gly | Thr | Arg | Leu | |
| | | 115 | | | | | 120 | | | | | 125 | | | | |
| tcc | atc | cta | gag | gac | ctg | aac | aag | gtg | ttc | cca | ccc | gag | gtc | gct | gtg | 432 |
| Ser | Ile | Leu | Glu | Asp | Leu | Asn | Lys | Val | Phe | Pro | Pro | Glu | Val | Ala | Val | |
| 130 | | | | | 135 | | | | | 140 | | | | | | |
| ttt | gag | cca | tca | gaa | gca | gag | atc | tcc | cac | acc | caa | aag | gcc | aca | ctg | 480 |
| Phe | Glu | Pro | Ser | Glu | Ala | Glu | Ile | Ser | His | Thr | Gln | Lys | Ala | Thr | Leu | |
| 145 | | | | 150 | | | | | 155 | | | | | 160 | | |
| gtg | tgc | ctg | gcc | aca | ggc | ttc | ttc | cct | gac | cac | gtg | gag | ctg | agc | tgg | 528 |
| Val | Cys | Leu | Ala | Thr | Gly | Phe | Phe | Pro | Asp | His | Val | Glu | Leu | Ser | Trp | |
| | | | | 165 | | | | | 170 | | | | | 175 | | |
| tgg | gtg | aat | ggg | aag | gag | gtg | cac | agt | ggg | gtc | agc | acg | gac | ccg | cag | 576 |
| Trp | Val | Asn | Gly | Lys | Glu | Val | His | Ser | Gly | Val | Ser | Thr | Asp | Pro | Gln | |
| | | | 180 | | | | | 185 | | | | | 190 | | | |
| ccc | ctc | aag | gag | cag | ccc | gcc | ctc | aat | gac | tcc | aga | tac | tgc | ctg | agc | 624 |
| Pro | Leu | Lys | Glu | Gln | Pro | Ala | Leu | Asn | Asp | Ser | Arg | Tyr | Cys | Leu | Ser | |
| | 195 | | | | | 200 | | | | | 205 | | | | | |
| agc | cgc | ctg | agg | gtc | tcg | gcc | acc | ttc | tgg | cag | aac | ccc | cgc | aac | cac | 672 |
| Ser | Arg | Leu | Arg | Val | Ser | Ala | Thr | Phe | Trp | Gln | Asn | Pro | Arg | Asn | His | |
| 210 | | | | | 215 | | | | | 220 | | | | | | |
| ttc | cgc | tgt | caa | gtc | cag | ttc | tac | ggg | ctc | tcg | gag | aat | gac | gag | tgg | 720 |
| Phe | Arg | Cys | Gln | Val | Gln | Phe | Tyr | Gly | Leu | Ser | Glu | Asn | Asp | Glu | Trp | |
| 225 | | | | 230 | | | | | 235 | | | | | 240 | | |
| acc | cag | gat | agg | gcc | aaa | ccc | gtc | acc | cag | atc | gtc | agc | gcc | gag | gcc | 768 |
| Thr | Gln | Asp | Arg | Ala | Lys | Pro | Val | Thr | Gln | Ile | Val | Ser | Ala | Glu | Ala | |
| | | | | 245 | | | | | 250 | | | | | 255 | | |
| tgg | ggt | aga | gca | gac | tgt | ggc | ttt | acc | tcg | gtg | tcc | tac | cag | caa | ggg | 816 |
| Trp | Gly | Arg | Ala | Asp | Cys | Gly | Phe | Thr | Ser | Val | Ser | Tyr | Gln | Gln | Gly | |
| | | | 260 | | | | | 265 | | | | | 270 | | | |
| gtc | ctg | tct | gcc | acc | atc | ctc | tat | gag | atc | ctg | cta | ggg | aag | gcc | acc | 864 |
| Val | Leu | Ser | Ala | Thr | Ile | Leu | Tyr | Glu | Ile | Leu | Leu | Gly | Lys | Ala | Thr | |
| | | 275 | | | | | 280 | | | | | 285 | | | | |
| ctg | tat | gct | gtg | ctg | gtc | agc | gcc | ctt | gtg | ttg | atg | gcc | atg | gtc | aag | 912 |
| Leu | Tyr | Ala | Val | Leu | Val | Ser | Ala | Leu | Val | Leu | Met | Ala | Met | Val | Lys | |
| | 290 | | | | | 295 | | | | | 300 | | | | | |
| aga | aag | gat | ttc | tga | | | | | | | | | | | | 927 |
| Arg | Lys | Asp | Phe | | | | | | | | | | | | | |
| 305 | | | | | | | | | | | | | | | | |

<210> SEQ ID NO 8
<211> LENGTH: 308
<212> TYPE: PRT
<213> ORGANISM: Homo sapiens

<400> SEQUENCE: 8

Met Asp Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala

```
                100             105             110
Ser Thr Ile Gly Ala Gln Pro Gln His Phe Gly Asp Gly Thr Arg Leu
        115                 120                 125

Ser Ile Leu Glu Asp Leu Asn Lys Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Phe
305

<210> SEQ ID NO 9
<211> LENGTH: 822
<212> TYPE: DNA
<213> ORGANISM: Homo sapiens
<220> FEATURE:
<221> NAME/KEY: CDS
<222> LOCATION: (1)..(822)

<400> SEQUENCE: 9 atg gtg aag atc cgg caa ttt ttg ttg gct att ttg tgg ctt cag cta      48
Met Val Lys Ile Arg Gln Phe Leu Leu Ala Ile Leu Trp Leu Gln Leu
1               5                   10                  15 agc tgt gta agt gcc gcc aaa aat gaa gtg gag cag agt cct cag aac      96
Ser Cys Val Ser Ala Ala Lys Asn Glu Val Glu Gln Ser Pro Gln Asn
                20                  25                  30 ctg act gcc cag gaa gga gaa ttt atc aca atc aac tgc agt tac tcg     144
Leu Thr Ala Gln Glu Gly Glu Phe Ile Thr Ile Asn Cys Ser Tyr Ser
            35                  40                  45 gta gga ata agt gcc tta cac tgg ctg caa cag cat cca gga gga ggc     192
Val Gly Ile Ser Ala Leu His Trp Leu Gln Gln His Pro Gly Gly Gly
        50                  55                  60 att gtt tcc ttg ttt atg ctg agc tca ggg aag aag aag cat gga aga     240
Ile Val Ser Leu Phe Met Leu Ser Ser Gly Lys Lys Lys His Gly Arg
65                  70                  75                  80 tta att gcc aca ata aac ata cag gaa aag cac agc tcc ctg cac atc     288
Leu Ile Ala Thr Ile Asn Ile Gln Glu Lys His Ser Ser Leu His Ile
                85                  90                  95 aca gcc tcc cat ccc aga gac tct gcc gtc tac atc tgt gct gcc tca     336
Thr Ala Ser His Pro Arg Asp Ser Ala Val Tyr Ile Cys Ala Ala Ser
                100                 105                 110
```

```
tta att cag gga gcc cag aag ctg gta ttt ggc caa gga acc agg ctg    384
Leu Ile Gln Gly Ala Gln Lys Leu Val Phe Gly Gln Gly Thr Arg Leu
        115                 120                 125 act atc aac cca aat atc cag aac cct gac cct gcc gtg tac cag ctg    432
Thr Ile Asn Pro Asn Ile Gln Asn Pro Asp Pro Ala Val Tyr Gln Leu
    130                 135                 140 aga gac tct aaa tcc agt gac aag tct gtc tgc cta ttc acc gat ttt    480
Arg Asp Ser Lys Ser Ser Asp Lys Ser Val Cys Leu Phe Thr Asp Phe
145                 150                 155                 160 gat tct caa aca aat gtg tca caa agt aag gat tct gat gtg tat atc    528
Asp Ser Gln Thr Asn Val Ser Gln Ser Lys Asp Ser Asp Val Tyr Ile
                165                 170                 175 aca gac aaa act gtg cta gac atg agg tct atg gac ttc aag agc aac    576
Thr Asp Lys Thr Val Leu Asp Met Arg Ser Met Asp Phe Lys Ser Asn
            180                 185                 190 agt gct gtg gcc tgg agc aac aaa tct gac ttt gca tgt gca aac gcc    624
Ser Ala Val Ala Trp Ser Asn Lys Ser Asp Phe Ala Cys Ala Asn Ala
        195                 200                 205 ttc aac aac agc att att cca gaa gac acc ttc ttc ccc agc cca gaa    672
Phe Asn Asn Ser Ile Ile Pro Glu Asp Thr Phe Phe Pro Ser Pro Glu
    210                 215                 220 agt tcc tgt gat gtc aag ctg gtc gag aaa agc ttt gaa aca gat acg    720
Ser Ser Cys Asp Val Lys Leu Val Glu Lys Ser Phe Glu Thr Asp Thr
225                 230                 235                 240 aac cta aac ttt caa aac ctg tca gtg att ggg ttc cga atc ctc ctc    768
Asn Leu Asn Phe Gln Asn Leu Ser Val Ile Gly Phe Arg Ile Leu Leu
                245                 250                 255 ctg aaa gtg gcc ggg ttt aat ctg ctc atg acg ctg cgg ctg tgg tcc    816
Leu Lys Val Ala Gly Phe Asn Leu Leu Met Thr Leu Arg Leu Trp Ser
            260                 265                 270 agc tga                                                            822
Ser

<210> SEQ ID NO 10
<211> LENGTH: 273
<212> TYPE: PRT
<213> ORGANISM: Homo sapiens

<400> SEQUENCE: 10

Met Val Lys Ile Arg Gln Phe Leu Leu Ala Ile Leu Trp Leu Gln Leu
1               5                   10                  15

Ser Cys Val Ser Ala Ala Lys Asn Glu Val Glu Gln Ser Pro Gln Asn
            20                  25                  30

Leu Thr Ala Gln Glu Gly Glu Phe Ile Thr Ile Asn Cys Ser Tyr Ser
        35                  40                  45

Val Gly Ile Ser Ala Leu His Trp Leu Gln Gln His Pro Gly Gly Gly
    50                  55                  60

Ile Val Ser Leu Phe Met Leu Ser Ser Gly Lys Lys His Gly Arg
65                  70                  75                  80

Leu Ile Ala Thr Ile Asn Ile Gln Glu Lys His Ser Ser Leu His Ile
                85                  90                  95

Thr Ala Ser His Pro Arg Asp Ser Ala Val Tyr Ile Cys Ala Ala Ser
            100                 105                 110

Leu Ile Gln Gly Ala Gln Lys Leu Val Phe Gly Gln Gly Thr Arg Leu
        115                 120                 125

Thr Ile Asn Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160
```

```
Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 11
<211> LENGTH: 933
<212> TYPE: DNA
<213> ORGANISM: Homo sapiens
<220> FEATURE:
<221> NAME/KEY: CDS
<222> LOCATION: (1)..(933)

<400> SEQUENCE: 11 atg gac tcc tgg acc ttc tgc tgt gtg tcc ctt tgc atc ctg gta gcg      48
Met Asp Ser Trp Thr Phe Cys Cys Val Ser Leu Cys Ile Leu Val Ala
1               5                   10                  15 aag cat aca gat gct gga gtt atc cag tca ccc cgc cat gag gtg aca      96
Lys His Thr Asp Ala Gly Val Ile Gln Ser Pro Arg His Glu Val Thr
                20                  25                  30 gag atg gga caa gaa gtg act ctg aga tgt aaa cca att tca ggc cac     144
Glu Met Gly Gln Glu Val Thr Leu Arg Cys Lys Pro Ile Ser Gly His
            35                  40                  45 aac tcc ctt ttc tgg tac aga cag acc atg atg cgg gga ctg gag ttg     192
Asn Ser Leu Phe Trp Tyr Arg Gln Thr Met Met Arg Gly Leu Glu Leu
        50                  55                  60 ctc att tac ttt aac aac aac gtt ccg ata gat gat tca ggg atg ccc     240
Leu Ile Tyr Phe Asn Asn Asn Val Pro Ile Asp Asp Ser Gly Met Pro
65                  70                  75                  80 gag gat cga ttc tca gct aag atg cct aat gca tca ttc tcc act ctg     288
Glu Asp Arg Phe Ser Ala Lys Met Pro Asn Ala Ser Phe Ser Thr Leu
                85                  90                  95 aag atc cag ccc tca gaa ccc agg gac tca gct gtg tac ttc tgt gcc     336
Lys Ile Gln Pro Ser Glu Pro Arg Asp Ser Ala Val Tyr Phe Cys Ala
            100                 105                 110 agc agc ccc ggg ggc aat gag cag ttc ttc ggg cca ggg aca cgg ctc     384
Ser Ser Pro Gly Gly Asn Glu Gln Phe Phe Gly Pro Gly Thr Arg Leu
        115                 120                 125 acc gtg cta gag gac ctg aaa aac gtg ttc cca ccc gag gtc gct gtg     432
Thr Val Leu Glu Asp Leu Lys Asn Val Phe Pro Pro Glu Val Ala Val
130                 135                 140 ttt gag cca tca gaa gca gag atc tcc cac acc caa aag gcc aca ctg     480
Phe Glu Pro Ser Glu Ala Glu Ile Ser His Thr Gln Lys Ala Thr Leu
145                 150                 155                 160 gta tgc ctg gcc aca ggc ttc tac ccc gac cac gtg gag ctg agc tgg     528
Val Cys Leu Ala Thr Gly Phe Tyr Pro Asp His Val Glu Leu Ser Trp
                165                 170                 175 tgg gtg aat ggg aag gag gtg cac agt ggg gtc agc aca gac ccg cag     576
```

-continued

```
Trp Val Asn Gly Lys Glu Val His Ser Gly Val Ser Thr Asp Pro Gln
            180                 185                 190 ccc ctc aag gag cag ccc gcc ctc aat gac tcc aga tac tgc ctg agc      624
Pro Leu Lys Glu Gln Pro Ala Leu Asn Asp Ser Arg Tyr Cys Leu Ser
        195                 200                 205 agc cgc ctg agg gtc tcg gcc acc ttc tgg cag aac ccc cgc aac cac      672
Ser Arg Leu Arg Val Ser Ala Thr Phe Trp Gln Asn Pro Arg Asn His
    210                 215                 220 ttc cgc tgt caa gtc cag ttc tac ggg ctc tcg gag aat gac gag tgg      720
Phe Arg Cys Gln Val Gln Phe Tyr Gly Leu Ser Glu Asn Asp Glu Trp
225                 230                 235                 240 acc cag gat agg gcc aaa ccc gtc acc cag atc gtc agc gcc gag gcc      768
Thr Gln Asp Arg Ala Lys Pro Val Thr Gln Ile Val Ser Ala Glu Ala
                245                 250                 255 tgg ggt aga gca gac tgt ggc ttc acc tcc gag tct tac cag caa ggg      816
Trp Gly Arg Ala Asp Cys Gly Phe Thr Ser Glu Ser Tyr Gln Gln Gly
            260                 265                 270 gtc ctg tct gcc acc atc ctc tat gag atc ttg cta ggg aag gcc acc      864
Val Leu Ser Ala Thr Ile Leu Tyr Glu Ile Leu Leu Gly Lys Ala Thr
        275                 280                 285 ttg tat gcc gtg ctg gtc agt gcc ctc gtg ctg atg gcc atg gtc aag      912
Leu Tyr Ala Val Leu Val Ser Ala Leu Val Leu Met Ala Met Val Lys
    290                 295                 300 aga aag gat tcc aga ggc tag                                          933
Arg Lys Asp Ser Arg Gly
305                 310

<210> SEQ ID NO 12
<211> LENGTH: 310
<212> TYPE: PRT
<213> ORGANISM: Homo sapiens

<400> SEQUENCE: 12

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Pro Gly Gly Asn Glu Gln Phe Phe Gly Pro Gly Thr Arg Leu
        115                 120                 125

Thr Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
```

```
            195                 200                     205
Ser Arg Leu Arg Val Ser Ala Thr Phe Trp Gln Asn Pro Arg Asn His
    210                 215                     220
Phe Arg Cys Gln Val Gln Phe Tyr Gly Leu Ser Glu Asn Asp Glu Trp
225                 230                     235                 240
Thr Gln Asp Arg Ala Lys Pro Val Thr Gln Ile Val Ser Ala Glu Ala
                245                 250                     255
Trp Gly Arg Ala Asp Cys Gly Phe Thr Ser Glu Ser Tyr Gln Gln Gly
            260                 265                     270
Val Leu Ser Ala Thr Ile Leu Tyr Glu Ile Leu Leu Gly Lys Ala Thr
        275                 280                     285
Leu Tyr Ala Val Leu Val Ser Ala Leu Val Leu Met Ala Met Val Lys
    290                 295                     300
Arg Lys Asp Ser Arg Gly
305                 310

<210> SEQ ID NO 13
<211> LENGTH: 9
<212> TYPE: PRT
<213> ORGANISM: Homo sapiens

<400> SEQUENCE: 13

Ser Leu Leu Met Trp Thr Thr Gln Cys
1               5

<210> SEQ ID NO 14
<211> LENGTH: 9
<212> TYPE: PRT
<213> ORGANISM: Homo sapiens

<400> SEQUENCE: 14

Ser Leu Leu Met Trp Thr Thr Gln Val
1               5

<210> SEQ ID NO 15
<211> LENGTH: 12
<212> TYPE: PRT
<213> ORGANISM: Homo sapiens

<400> SEQUENCE: 15

Ser Leu Leu Met Trp Thr Thr Gln Cys Phe Leu Pro
1               5                   10

<210> SEQ ID NO 16
<211> LENGTH: 20
<212> TYPE: PRT
<213> ORGANISM: Homo sapiens

<400> SEQUENCE: 16

Trp Ile Thr Gln Cys Phe Leu Pro Val Phe Leu Ala Gln Pro Pro Ser
1               5                   10                  15
Gly Gln Arg Ala
            20

<210> SEQ ID NO 17
<211> LENGTH: 9
<212> TYPE: PRT
<213> ORGANISM: Homo sapiens

<400> SEQUENCE: 17

Ile Thr Asp Gln Val Pro Phe Ser Val
1               5
```

```
<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Ile Met Asp Gln Val Pro Phe Ser Val
1               5

<210> SEQ ID NO 19
<211> LENGTH: 10
<212> TYPE: PRT
<213> ORGANISM: Artificial Sequence
<220> FEATURE:
<223> OTHER INFORMATION: Synthetic

<400> SEQUENCE: 19

Glu Ala Ala Gly Ile Gly Ile Leu Thr Leu
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic

<400> SEQUENCE: 20

Glu Leu Ala Gly Ile Gly Ile Leu Thr Leu
1               5                   10
```